United States Patent [19]

Rotini et al.

[11] Patent Number: 5,043,167

[45] Date of Patent: Aug. 27, 1991

[54] GALENIC FORMULATIONS WITH PROGRAMMED RELEASE

[75] Inventors: Leone G. Rotini; Egidio Marchi, both of Bologna, Italy

[73] Assignee: Alfa Wassermann S.p.A., Pescara, Italy

[21] Appl. No.: 293,670

[22] Filed: Jan. 5, 1989

[30] Foreign Application Priority Data

Jan. 18, 1988 [IT] Italy .................... 19100 A/88

[51] Int. Cl.⁵ .................... A61K 9/16; A61K 9/22; A61K 9/52
[52] U.S. Cl. .................... 424/490; 424/494; 424/451; 424/456; 424/464; 424/479; 424/459; 424/489
[58] Field of Search ............... 424/494, 451, 456, 464, 424/479, 459, 489

[56] References Cited

U.S. PATENT DOCUMENTS 4,765,990 8/1988 Sugimoto et al. .................... 424/494

Primary Examiner—Thurman K. Page
Assistant Examiner—R. Harrison
Attorney, Agent, or Firm—Birch, Stewart, Kolasch & Birch

[57] ABSTRACT

New galenic formulations with programmed release, to be administered by the oral route, containing as the active ingredient a drug selected from the non steroidal antiinflammatory, bronchodilator, vasodilator, cardiovascular and muscle relaxant drugs.

8 Claims, No Drawings

GALENIC FORMULATIONS WITH PROGRAMMED RELEASE

BACKGROUND OF THE INVENTION

The art skilled man knows well the problems connected with the repeated administration of drugs. Apart from the trouble and the discomfort, mostly psychologic, which the patient can experience when he has to recollect of taking that determinate medicine three or four times a day (as it happens, for instance, with paracetamol), it must be born in mind that, from the point of view of the absorption kinetics, repeated administration is responsible of very high hematic levels of the drug which repeatedly occur in the organism of the patient, with a remarkable increase in the possibility of side effects. In the literature many methodologies are described, generically called "retard", by means of which the number of administrations of a drug can be reduced while keeping unaltered its therapeutic effectiveness during time.

Thus, for instance, slow-release tablets of indomethacin, where the active principle is coated by a film of a hydrophilic polymer and by a cellulose ether, are claimed in Japanese laid open application J 58170712, while in Japanese laid open application J 59084821, diclofenac, which is another well known antiphlogistic agent, is mixed with $\beta$-cyclodestrin. In German laid open application DE 3001797, indoprofen, a good analgesic and antiinflammatory agent which has the drawback of having a short plasma half-life, is microencapsulated in a protective layer of a cellulose ether, thus obtaining a remarkable improvement of its plasma half-life. Finally, in European publications EP 0094116, EP 0094117 and EP 0094123, granules are described which have a double coating, the first made of polyvinylpyrrolidone and the second one made of acrylic polymers or by cellulose esters or by fatty or oily substances, which should allow a better release of antiphlogistic drugs either in the stomach and in the gut.

In all of these galenic formulations, however, the initial release of the active ingredient is gradual and slow, so that the therapeutic effect begins only some hours after administration. This is an evident drawback, especially in the case of drugs which contemporaneously present antiinflammatory, analgesic and antipyretic activity, where often a quick release is needed in order to obtain a prompt analgesic effect, besides the slow and regular release in order to cure the inflammation.

SUMMARY OF THE INVENTION

Object of the present invention are new galenic formulations with programmed release, immediate and delayed. These formulations are administered by the oral route and contain, as the active principle, a drug selected from non steroidal antiinflammatory, bronchodilator, vasodilator, cardiovascular and muscle relaxant drugs.

In order to remove the drawbacks of the known controlled release formulations, and in order to obtain an adequate therapeutic response since the beginning, the galenic formulations of the present invention are made by a mixture of a granulate having an immediate release with a granulate having a controlled release, in terms of active ingredient. In this way, by suitably selecting both the kind and the amount of the agents to be used in the manufacture of the two granulates, and the weight ratio between the two types of granulate, it is possible to obtain pharmaceutical formulations having an immediate therapeutic activity which protracts along 12-24 hours, being therefore suitable for a once a day administration.

This effect is due to the particular structure that the joining of the two granulates gives to the galenic preparations. It was really found that the galenic formulations of the present invention disintegrate in such a manner that they release microgranules some of which, being made from the immediate release granulate, are quickly adsorbed by the body, while the others, being made from the controlled release granulate, provide the active principle over a long period of time when they get in contact with an aqueous medium like, for instance, water itself or acidic aqueous solutions or aqueous solutions which simulate the gastric juices or the gastric juice itself. The great advantage of these galenic formulations with respect to the usual delayed formulations is that, in the present invention, there is no great local concentration of drug as it homogenously disperses into the medium in which it will be adsorbed, because of the disintegration in microgranules of the formulation in which the drug is incorporated. A further object of the invention is therefore represented by the particular kind of galenic support where the active principle can be incorporated.

This galenic support is characterized in that it disintegrates into in microgranules which are suitable both for the immediate and the delayed release of the active principle which can be incorporated in them. Each of these microgranules has a diameter of not greater than one millimetre. In this support, the microgranules suitable for the immediate release of the active principle are in an amount comprised between about 5% and about 40% of the total weight of the support, while the microgranules suitable for the delayed release are in an amount comprised between about 60% and about 95% of the total weight of the support. In the experimental tests carried out on the formulations of the present invention, we found that the best therapeutic response was obtained when the active principle was contained in an amount between about 15% and about 85% in weight of the total weight of the active principle itself, both in the immediate release granulate and in the controlled release granulate.

The drugs preferred in carrying out the present invention are the non steroidal antiinflammatory drugs and the bronchodilators, particularly preferred are the sodium salts of naproxen and diclofenac and the bamifylline hydrochloride.

Tablets, capsules, sugar coated tablets and granulates for suspension or for solution in suitable liquid media are the preferred galenic formulations.

The preparation of the galenic formulations of the present invention is hereinafter described, being evident for the man skilled in the art that the excipients used in the preparation of the granulates are the same which constitute the galenic support, which is also the object of the present invention.

In the preparation of the galenic formulations of the present invention, the immediate release granulate is prepared by wet granulating the active principle with suitable adjuvants such as binding, disintegrating and lubricating agents, then drying the obtained granulate in an oven at 50° C. for about 4 hours the granules and lastly sifting on a sieve having mesh of 1 mm.

Polyvinylpyrrolidone, carboxymethylcellulose, microcrystalline cellulose, lactose, saccharose, mannitol, gumarabic, pectin and gelatin can be advantageously used as binding agents.

Starch, sodium starch glycolate, alginates and reticulated polyvinylpirrolidone can be used as disintegrating agents.

Talc, magnesium stearate, stearic acid and silica gel can be used as lubricating agents.

Polyvinylpyrrolidone, lactose, maize starch, sodium starch glycolate and magnesium stearate are the preferred adjuvants in the present invention.

The granulate having a controlled release, is prepared by wet granulating the active principle together with retarding agents, drying the granules in oven at 50° C. and sifting them through a sieve having mesh of 1 mm.

Many retarding agents can be advantageously used; they are preferably selected among ethylcellulose, methylcellulose, polyvinylacetate, methacrylic acid esters, cellulose acetate, fatty alcohols containing from 12 to 32 carbon atoms, glycerol esters of fatty acids containing from 10 to 22 carbon atoms, like the mono- and di-stearate of glycerol, esters of fatty acids and alcohols having from 12 to 31 carbon atoms, paraffin, natural waxy substances like beeswax, unbleached wax, candelilla wax, carnauba wax, sealing wax, spermaceti, ozokerite and hydrogenated vegetable oils like hydrogenated castor oil, hydrogenated peanut oil, hydrogenated cotton seed oil and mixtures thereof.

Methylcellulose, ethylcellulose, hydrogenated vegetable oils and mixtures thereof are the retarding agents preferred in the present invention.

The solvents used for the wet granulation are selected from an alcohol containing from 1 to 4 carbon atoms, an aromatic hydrocarbon, a ketone containing from 3 to 6 carbon atoms, an alkyl halide containing from 1 to 4 carbon atoms, mixtures thereof or mixtures thereof with water. Alcohols containing from 1 to 4 carbon atoms and their mixtures with water are the preferred solvents, mostly 95% ethyl alcohol.

In the preparation of the desired galenic formulation, carried out according to known techniques, the two granulates are mixed in such weight ratios that the active principle contained in the final galenic formulation belongs to each one of two granulates for a percent comprised between about 15% and about 85% of the whole active principle.

The granulate having immediate release, contains from about 45% to about 90% of active principle, from about 2% to about 20% of binding agents, from about 5% to about 40% of disintegrating agents and up to about 1% of a lubricating agent.

The granulate having controlled release contains from about 40% to about 60% of active principle and from about 40% to about 60% of a retarding agent or of a mixture of retarding agents.

Some examples of galenic formulations obtained according to that previously said, are hereinafter described to illustrate the invention; nevertheless such examples are not to be interpreted as a limitation of the invention itself.

EXAMPLE 1

Tablets containing 412.5 mg-550 mg-775 mg-1100 mg of Sodium Naproxen

Immediate Release Granulate

300 Grams of sodium naproxen, 30 g of sodium starch glycolate, 20 g of maize starch, 30 g of polyvinylpyrrolidone, 20 g of lactose and 4 g of magnesium stearate are mixed and wet granulated with 90 ml of 95% ethyl alcohol. The granules are then dried in an oven at 50° C. for 4 hours and subsequently sifted on a sieve having mesh of 1 mm.

Controlled Release Granulate

800 Grams of sodium naproxen, 480 g of hydrogenated castor oil and 160 g of ethylcellulose are mixed and wet granulated with 500 ml of 95% ethyl alcohol. The granules are then dried in an oven at 50° C. for 4 hours and then sifted on a sieve having mesh of 1 mm.

Tablets

The two granulates are carefully mixed and the resulting mixture is put into the compressed tablet machine where it is pressed under a 800 kg/cm$^2$ pressure, so obtaining tablets having the average weight of 691.5 mg for the dose of 412.5 mg of sodium naproxen, the average weight of 922 mg for the dose of 550 mg of sodium naproxen, the average weight of 1383 mg for the dose of 775 mg of sodium naproxen and the average weight of 1844 mg for the dose of 1100 mg of sodium naproxen.

Some of these tablets were submitted to an in vitro test of release of the active principle in water, by using an apparatus according to the standards of the IX Edition of the Italian Official Pharmacopoeia.

The data related to the release of the active principle are listed in the table below.

TABLE 1

| Time of release | % of sodium naproxen released |
| --- | --- |
| 10 minutes | 17.7 |
| 20 minutes | 22.7 |
| 30 minutes | 30.0 |
| 1 hour | 37.7 |
| 2 hours | 53.0 |
| 3 hours | 66.6 |
| 4 hours | 82.5 |
| 6 hours | 95.8 |
| 8 hours | 100 |

EXAMPLE 2

Tablets Containing 50 mg-75 mg-100 mg-150 mg of Sodium Diclofenac

Immediate Release Granulate

50 Grams of sodium diclofenac, 10 g of polyvinylpirrolidone, 20 g of sodium starch glycolate, 10 g of lactose and 20 g of maize starch are mixed and wet granulated with 20 ml of 95% ethyl alcohol. The granules are dried in an oven at 50° C. for 4 hours and then sifted on a sieve having mesh of 1 mm.

Controlled Release Granulate

150 Grams of sodium diclofenac, 120 g of hydrogenated castor oil and 40 g of ethylcellulose are mixed and wet granulated with 90 ml of 95% ethyl alcohol. The granules are dried in an oven at 50° C. for 4 hours and then sifted on a sieve having mesh of 1 mm.

Tablets

The two granulates are carefully mixed and the resulting mixture is put into the compressed tablet machine where it is pressed under a 700 kg/cm$^2$ pressure, so obtaining tablets having the average weight of 105 mg for the dose of 50 mg of sodium diclofenac, the average weight of 157.5 mg for the dose of 75 mg of sodium diclofenac, the average weight of 210 mg for the dose of 100 mg of sodium diclofenac and the average weight of 315 mg for the dose of 150 mg of sodium diclofenac.

Some of these tablets were submitted to an in vitro test of release of the active principle in water as in example 1. The data related to the release of the active principle are listed in the table below.

TABLE 2

| Time of release | % of sodium diclofenac released |
| --- | --- |
| 10 minutes | 18.5 |
| 20 minutes | 23.0 |
| 30 minutes | 27.5 |
| 1 hour | 38.9 |
| 2 hours | 53.9 |
| 3 hours | 67.3 |
| 4 hours | 77.7 |
| 6 hours | 83.1 |
| 8 hours | 91.5 |

EXAMPLE 3

Tablets Containing 600 mg-900 mg-1200 mg of Bamifylline Hydrochloride

Immediate Release Granulate

360 Grams of bamifylline hydrochloride, 20 g of sodium starch glycolate, 6 g of polyvinylpirrolidone, 4 g of lactose, 4 g of maize starch and 4 g of magnesium stearate are mixed and wet granulated with 90 ml of 95% ethyl alcohol. The granules are dried in an oven at 50° C. for 4 hours and then sifted on a sieve having mesh of 1 mm.

Controlled Release Granulate

840 Grams of bamifylline hydrochloride, 532 g of hydrogenated castor oil and 168 g of ethylcellulose are mixed and wet granulated with 500 ml of 95% ethyl alcohol. The granules are dried in an oven at 50° C. for 4 hours and then sifted on a sieve having mesh of 1 mm.

Tablets

The two granulates are carefully mixed and the resulting mixture is put into the compressed tablet machine where it is pressed under a 800 kg/cm² pressure, so obtaining tablets having the average weight of 969 mg for the dose of 600 mg of bamifylline hydrochloride, the average weight of 1453.5 mg for the dose of 900 mg of bamifylline hydrochloride and the average weight of 1938 mg for the dose of 1200 mg of bamifylline hydrochloride.

Some of these tablets were submitted to an in vitro test of release of the active principle in water by operating as in example 1.

The data related to the release of the active principle are listed in the table below.

TABLE 3

| Time of release | % of bamifylline hydrochloride released |
| --- | --- |
| 10 minutes | 13.3 |
| 20 minutes | 20.8 |
| 30 minutes | 21.6 |
| 1 hour | 37.4 |
| 2 hours | 50.3 |
| 3 hours | 61.0 |
| 4 hours | 68.8 |
| 6 hours | 83.7 |

TABLE 3-continued

| Time of release | % of bamifylline hydrochloride released |
| --- | --- |
| 8 hours | 91.0 |

EXAMPLE 4

Capsules Containing 412.5 mg of Sodium Naproxen 20.2 Grams of immediate release granulate and 40.5 g of controlled release granulate prepared according to the example 1 are carefully mixed and the resulting mixture is used to fill up gelatine capsules each containing 412.5 mg of sodium naproxen.

EXAMPLE 5

Sugar Coated Tablets Containing 75 mg of Sodium Diclofenac 5.50 Grams of immediate release granulate and 10.33 g of controlled release granulate prepared according to example 2 are carefully mixed and the resulting mixture is used for the production, according to known techniques, of sugar coated tablets each containing 75 mg of sodium diclofenac.

EXAMPLE 6

Granulate for Solution or Suspension Containing 900 mg of Bamifylline Hydrochloride 39.8 Grams of immediate release granulate and 99 g of controlled release granulate prepared according to example 3 are carefully mixed together with 200 g of orange granulate and the resulting mixture is used to fill up granulate packets each containing 900 mg of bamifylline hydrochloride.

We claim:

1. A Galenic programmed release formulation for oral use containing as the active principle an active agent selected from the group consisting of sodium dicloflenac, sodium naproxen, and bamifylline hydrochloride, which comprises a mixture of (a) granulates having immediate release containing said active principle in an amount of from about 15% to about 85% of the total amount of said active principle present in said formulation together with binding, disintegrating and lubricating agents and (b) granulates having controlled release containing said active principle in an amount of from about 15% to about 85% of the total amount of said active principle present in said formulation together with at least one retarding agent.

2. The Galenic formulation according to claim 1 wherein said granulates having immediate release contain from about 45% to about 90% of active principle, from about 2% to about 20% of binding agents, and from about 5% to about 40% of disintegrating agents and up to about 1% of lubricating agents.

3. The Galenic formulation according to claim 1 wherein said granulates having controlled release contain from about 40% to about 60% of active principle and from about 40% to about 60% of a retarding agent or of a mixture of retarding agents.

4. The Galenic formulation according to any one of the preceding claims, wherein said binding agents are selected from polyvinylpyrrolidone, carboxymethylcellulose, microcrystalline cellulose, lactose, saccharose, mannitol, arabic gum, pectin and gelatin; said disintegrating agents are selected from starchs, alginates, sodium starch glycolate and reticulated polyvinylpyrrolidone; said lubricating agents are selected from magnesium stearate, talc, stearic acid and silica gel; and said retarding agents are selected from ethylcellulose, methylcellulose, polyvinylacetate, methacrylic acid esters, cellulose acetate, fatty alcohols containing from 10 to 32 carbon atoms, glycerol esters of fatty acids containing from 10 to 22 carbon atoms, esters of fatty acids and alcohols having from 12 to 31 carbon atoms, paraffin, beeswax, unbleached wax, candelilla wax, carnauba wax, sealing wax, spermaceti, ozokerite, hydrogenated castor oil, hydrogenated peanut oil, hydrogenated cotton seed oil and mixtures thereof.

5. The Galenic formulation according to claim 4, wherein said binding agents are lactose and polyvinylpyrrolidone, said disintegrating agents are maize starch and sodium starch glycolate, said lubricating agent is magnesium stearate and said retarding agents are ethylcellulose and hydrogenated castor oil.

6. The Galenic formulation according to any one of claims 1, 2, 3 or 5 in the form of tablets, sugar coated tablets, capsules and granulates for solution or suspension.

7. The Galenic formulation according to claim 6 wherein said granulates have an average diameter of not greater than 1 millimeter.

8. The galenic formulation according to claim 6 wherein said immediate release granulates are present in an amount of from 5 to 40% by weight based on the total weight of the formulation, and said delayed released granulates are present in an amount of from 60 to 95% by weight, based on the total weight of the formulation.

* * * * *